(12) United States Patent
Avent et al.

(10) Patent No.: US 8,479,413 B2
(45) Date of Patent: Jul. 9, 2013

(54) FOOTWEAR INSOLE FOR ALLEVIATING ARTHRITIS PAIN

(75) Inventors: Richard T. Avent, Memphis, TN (US); Jane M. Cappaert, Bartlett, TN (US); Charles E. Lundy, Jr., Germantown, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 781 days.

(21) Appl. No.: 12/341,474

(22) Filed: Dec. 22, 2008

(65) Prior Publication Data

US 2010/0154252 A1  Jun. 24, 2010

(51) Int. Cl.
*A43B 13/38* (2006.01)
*A43B 7/14* (2006.01)

(52) U.S. Cl.
USPC ........................ 36/44; 36/108; 36/88

(58) Field of Classification Search
USPC ............. 36/43, 44, 71, 108, 154, 88, 93, 140, 36/107
See application file for complete search history.

(56) References Cited

U.S. PATENT DOCUMENTS

| | | | |
|---|---|---|---|
| 4,317,293 A | 3/1982 | Sigle et al. | |
| 4,338,734 A * | 7/1982 | Schwartz | 36/44 |
| 5,068,983 A | 12/1991 | Marc | |
| 5,077,915 A * | 1/1992 | Gross | 36/31 |
| 5,146,698 A | 9/1992 | Tilles et al. | |
| 5,611,153 A | 3/1997 | Fisher et al. | |
| 6,125,557 A | 10/2000 | Brown | |
| 6,233,847 B1 | 5/2001 | Brown | |
| 6,269,555 B1 | 8/2001 | Brown | |
| 6,481,120 B1 | 11/2002 | Xia et al. | |
| 6,502,330 B1 | 1/2003 | David et al. | |
| 6,510,626 B1 | 1/2003 | Greenawalt | |
| 6,601,320 B1 | 8/2003 | Brown | |
| 6,618,960 B2 | 9/2003 | Brown | |
| 6,732,456 B2 | 5/2004 | Hussain | |
| 6,745,501 B2 | 6/2004 | Brown | |
| 7,124,518 B1 | 10/2006 | Brown | |
| 7,200,955 B2 * | 4/2007 | Foxen | 36/25 R |
| 7,284,342 B2 | 10/2007 | Avent et al. | |
| 7,380,353 B2 * | 6/2008 | Feller et al. | 36/76 R |

(Continued)

FOREIGN PATENT DOCUMENTS

| | | |
|---|---|---|
| DE | 20 2007 008016 U1 | 9/2007 |
| DE | 20 2007 013 671 U1 | 1/2008 |
| WO | WO 95/00047 | 1/1995 |
| WO | WO 2008/129389 | 10/2008 |

OTHER PUBLICATIONS

Baker, Kristin et al., "A Randomized Crossover Trial of a Wedged Insole for Treatment of Knee Osteoarthritis", Arthritis & Rheumatism, vol. 56, No. 4, pp. 1198-1203, (2007).

(Continued)

*Primary Examiner* — Jila M Mohandesi
(74) *Attorney, Agent, or Firm* — Dianne Pecoraro; Matthew J. Golden; Catherine D. Fitch

(57) ABSTRACT

Disclosed is a footwear insole for alleviating arthritis pain of the foot, knee, and/or hip by providing a rigid shell layer for arch support, and a topcloth, an upper cushioning layer, and a lower cushioning layer for cushioning. Further, the rigid shell layer includes a shell aperture, and the lower cushioning layer includes a lower layer aperture, through which a portion of the upper cushioning layer extends for cushioning.

22 Claims, 15 Drawing Sheets

U.S. PATENT DOCUMENTS

| | | | |
|---|---|---|---|
| 7,484,319 B2* | 2/2009 | Cheskin et al. | 36/44 |
| 7,707,751 B2* | 5/2010 | Avent et al. | 36/150 |
| 7,958,653 B2* | 6/2011 | Howlett et al. | 36/44 |
| 2002/0050080 A1 | 5/2002 | Vasyli | |
| 2003/0009915 A1 | 1/2003 | Bacon | |
| 2003/0140523 A1* | 7/2003 | Issler | 36/37 |
| 2004/0181976 A1* | 9/2004 | Copeskey et al. | 36/145 |
| 2004/0194344 A1* | 10/2004 | Tadin | 36/44 |
| 2005/0268490 A1 | 12/2005 | Foxen | |
| 2007/0107251 A1* | 5/2007 | Goldberg et al. | 34/82 |
| 2007/0107261 A1* | 5/2007 | Cheskin et al. | 36/44 |
| 2007/0277400 A1 | 12/2007 | Nguyen | |
| 2007/0289170 A1 | 12/2007 | Avent et al. | |
| 2008/0010861 A1 | 1/2008 | Kosmas | |
| 2008/0072461 A1 | 3/2008 | Howlett et al. | |
| 2009/0049712 A1* | 2/2009 | Steszyn et al. | 36/91 |

OTHER PUBLICATIONS

Kerrigan, Casey D., et al., "Effectiveness of a Lateral-Wedge Insole on Knee Varus Torque in Patients With Knee Osteoarthritis", Arch Phys Med Rehabil, vol. 83, pp. 889-893, (2002).

PCT Written Opinion for corresponding International Application PCT/US2009/068645; (7 pages).

International Search Report for corresponding International Application PCT/US2009/068645, mailed Mar. 19, 2010 (6 pages).

* cited by examiner

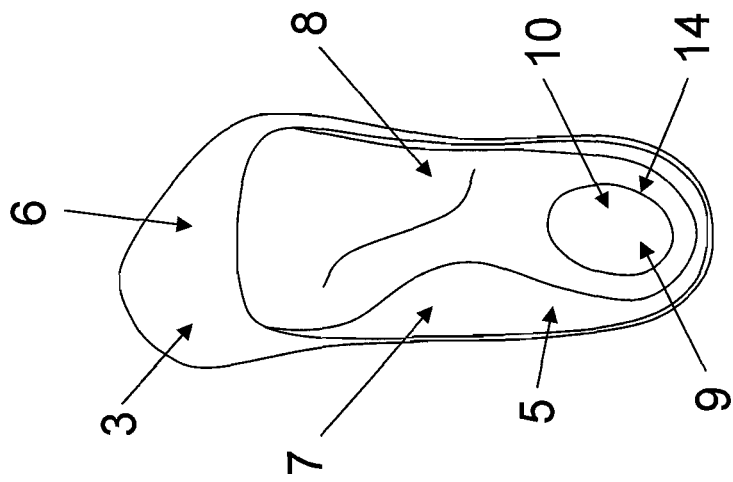
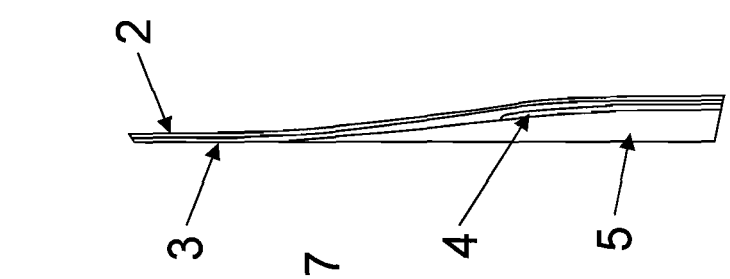
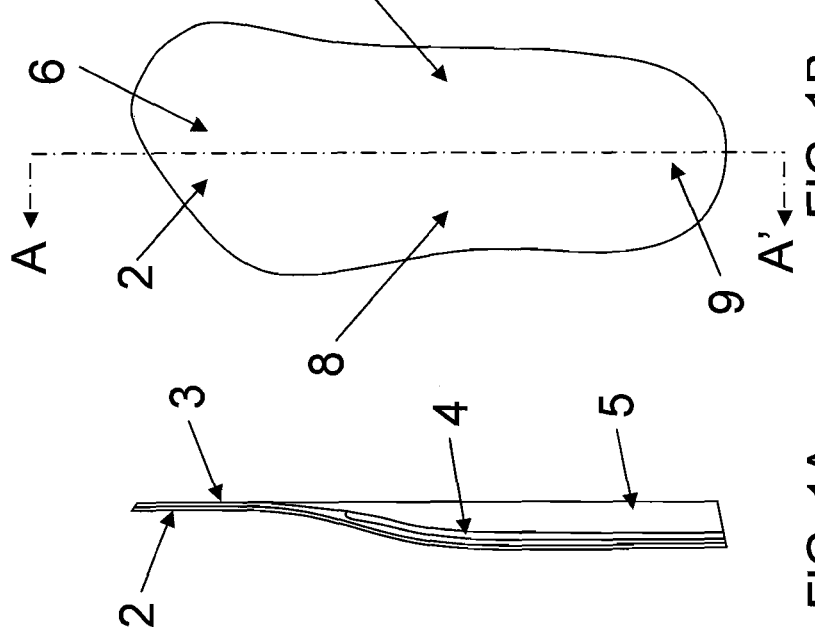
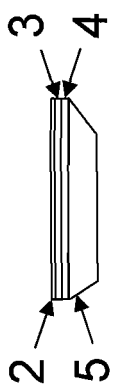
FIG. 1D
FIG. 1C
FIG. 1E
FIG. 1B
FIG. 1A

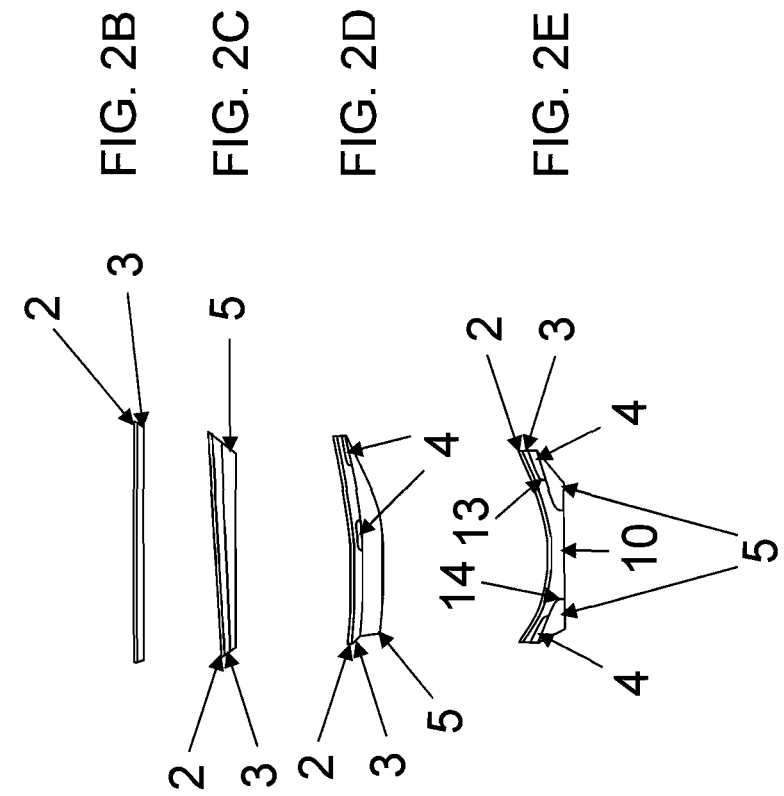
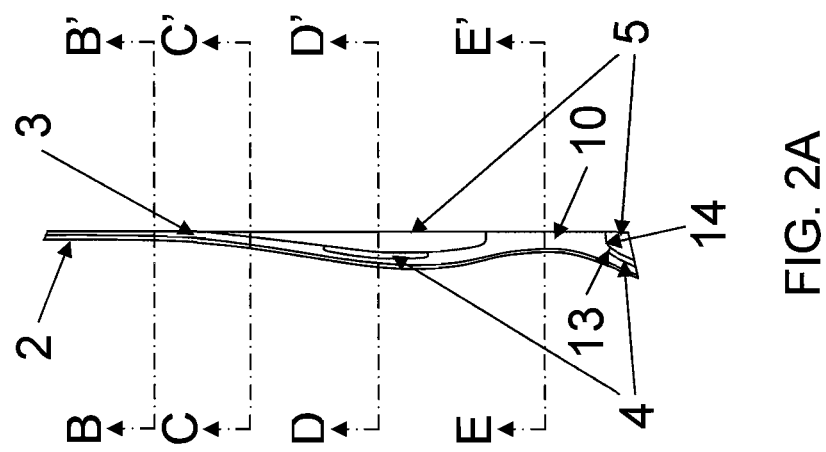

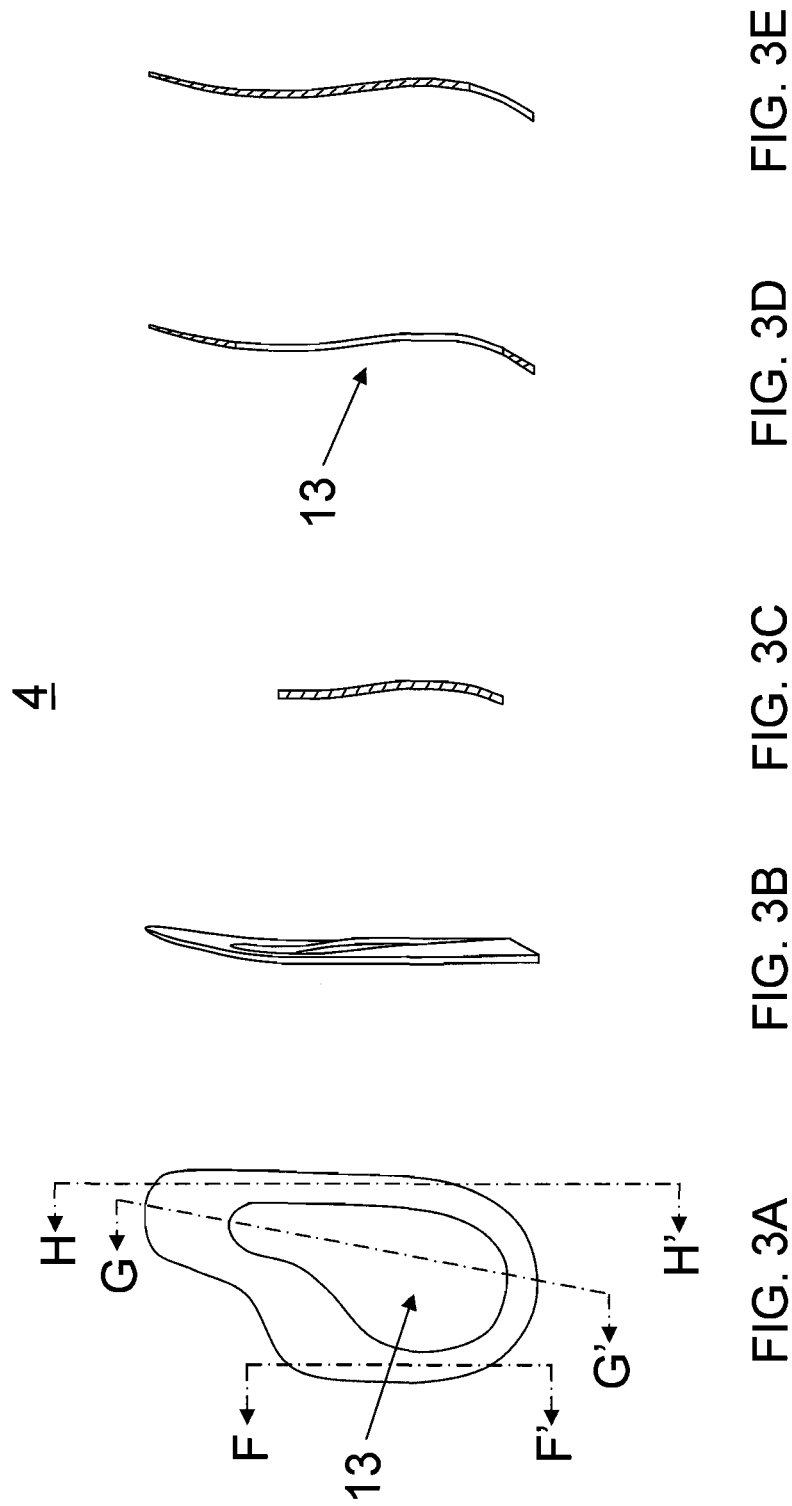

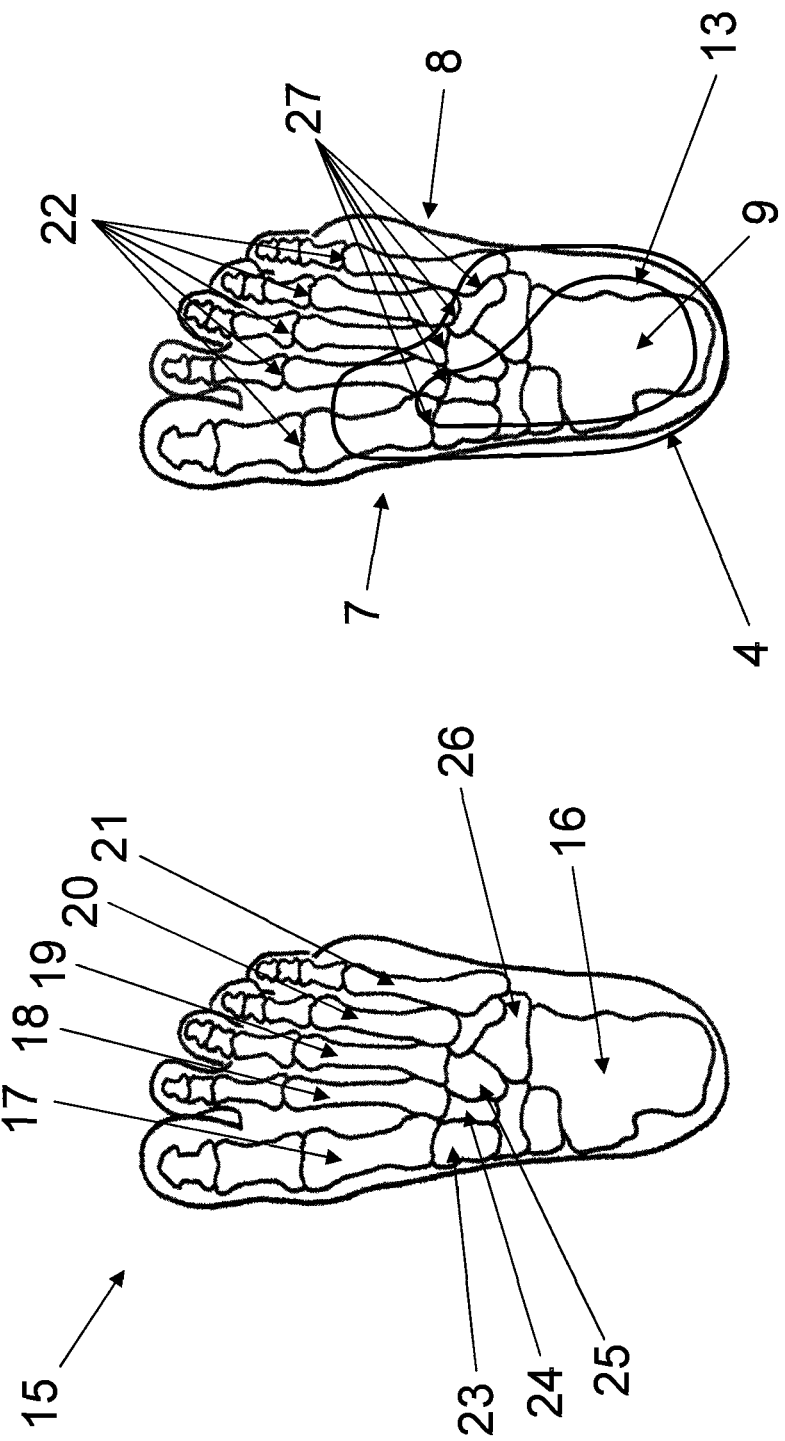

Arthritis Pain Test Subjects

| Gender | Arthritis Site | Test Site 1 | Test Site 2 | Combined |
|---|---|---|---|---|
| Male | Foot | 24 | 13 | 37 |
| Male | Hip | 9 | 9 | 18 |
| Male | Knee | 28 | 16 | 44 |
| Female | Foot | 17 | 26 | 43 |
| Female | Hip | 22 | 20 | 42 |
| Female | Knee | 21 | 23 | 44 |

FIG. 5

Test Results for Subjects Having Arthritis Pain in the Knee

| | Baseline | Immediate | 8 hours | Week 1 | Week 2 | Week 3 |
|---|---|---|---|---|---|---|
| Males<br>VAS score and<br>% reduction<br>n = 44 | 4.955 | 4.582<br>7.53%<br>p = .0031 | 4.073<br>17.8%<br>p < .0001 | 3.808<br>23.1%<br>p < .0001 | 3.453<br>30.3%<br>p < .0001 | 2.882<br>41.8%<br>p < .0001 |
| Females<br>VAS score and<br>% reduction<br>n = 44 | 5.099 | 4.719<br>7.50%<br>p = .0132 | 4.250<br>16.65%<br>p < .0001 | 3.713<br>27.2%<br>p < .0001 | 3.360<br>34.1%<br>p < .0001 | 2.922<br>42.7%<br>p < .0001 |

FIG. 6A

Test Results for Subjects Having Arthritis Pain in the Knee

| | Baseline | Immediate | 8 hour | Week 1 | Week 2 | Week 3 |
|---|---|---|---|---|---|---|
| Men Test Site 2 % red. and sig. | 5.109 n = 16 | 4.728 7.46% p = .1481 | 4.366 14.5% p = .0312 | 4.019 21.3% p = .0068 | 3.856 24.5% p = .0115 | 3.259 36.2% p = .0063 |
| Men Test Site 1 % red. and sig. | 4.866 n = 28 | 4.498 7.56% p = .0120 | 3.905 19.7% p <.0001 | 3.687 24.2% p <.0001 | 3.223 33.8% p <.0001 | 2.666 45.2% p <.0001 |
| Women Test Site 2 % red. and sig. | 5.126 n = 23 | 5.176 -.97% p = .5586 | 4.611 10.0% p = .0032 | 4.096 20.1% p = .0169 | 3.57 30.4% p = .0002 | 3.307 35.5% p <.0001 |
| Women Test Site 1 % red. and sig. | 5.069 n = 21 | 4.219 16.8% p = .0038 | 3.855 23.9% p = .0011 | 3.293 35.0% p <.0001 | 3.131 38.2% p <.0001 | 2.500 50.7% p <.0001 |

FIG. 6B

Test Results for Subjects Having Arthritis Pain in the Foot

| | Baseline | Immediate | 8 hours | Week 1 | Week 2 | Week 3 |
|---|---|---|---|---|---|---|
| Males<br>VAS score and<br>% reduction<br>n = 37 | 5.264 | 4.734<br>7.6%<br>P <.0001 | 4.661<br>8.82%<br>P =<br>.0002 | 4.177<br>20.4%<br>P <<br>.0001 | 3.551<br>30.0%<br>P <<br>.0001 | 3.061<br>40.8%<br>P <<br>.0001 |
| Females<br>VAS score and<br>% reduction<br>n = 42 | 5.673 | 4.811<br>15.2%<br>P = .0006 | 4.707<br>17.0%<br>P =<br>.0004 | 3.934<br>30.7%<br>P <<br>.0001 | 3.466<br>38.9%<br>P <<br>.0001 | 3.124<br>44.9%<br>P <<br>.0001 |

FIG. 7A

Test Results for Subjects Having Arthritis Pain in the Foot

| | Baseline | Immediate | 8 hour | Week 1 | Week 2 | Week 3 |
|---|---|---|---|---|---|---|
| Men Test Site 2 % red. and sig. | 5.446 n = 13 | 5.115 6.1% p = .0255 | 4.792 12.0% p = .0025 | 4.454 18.2% p = .0067 | 3.938 27.7% p < .0001 | 3.323 40.0% p = .0002 |
| Men Test Site 1 % red. and sig. | 5.165 n = 24 | 4.527 12.4% p = .0001 | 4.590 11.1% p = .0120 | 4.027 22.0% p = .0007 | 3.342 35.3% p < .0001 | 2.919 43.5% p < .0001 |
| Women Test Site 2 % red. and sig. | 6.465 n = 26 | 5.373 16.9% p = .0042 | 5.365 17.0% p = .0043 | 4.256 34.2% p < .0001 n = 25 | 3.796 41.3% p < .0001 n = 25 | 3.269 49.4% p < .0001 n = 26 |
| Women Test Site 1 % red. and sig. | 4.384 n = 16 | 3.897 11.1% p = .0378 | 3.638 17.0% p = .0389 | 3.431 21.7% p = .0066 | 2.950 32.7% p = .0016 | 2.888 34.1% p = .0036 |

FIG. 7B

Test Results for Subjects Having Arthritis Pain in the Hip

| | Baseline | Immediate | 8 hours | Week 1 | Week 2 | Week 3 |
|---|---|---|---|---|---|---|
| Males<br>VAS score and<br>% reduction<br>n = 18 | 5.225 | 4.619<br>11.6%<br>P = .0253 | 4.278<br>18.1%<br>P = .0107 | 3.992<br>23.6%<br>P = .0037 | 4.083<br>21.9%<br>P = .0231 | 3.969<br>24.0%<br>P = .0068 |
| Females<br>VAS score and<br>% reduction<br>n = 42 | 4.779 | 4.183<br>12.5%<br>p = .0003 | 3.695<br>22.7%<br>p < .0001 | 3.227<br>32.5%<br>p < .0001 | 2.821<br>41.0%<br>p = .0001 | 2.349<br>50.8%<br>p < .0001 |

FIG. 8A

Test Results for Subjects Having Arthritis Pain in the Hip

| | Baseline | Immediate | 8 hour | Week 1 | Week 2 | Week 3 |
|---|---|---|---|---|---|---|
| Men Test Site 2 % red. and sig. | 5.367 n = 9 | 4.778 11.0% p = .2083 | 4.456 17.0% p = .1516 | 4.589 14.5% p = .2136 | 4.511 15.9% p = .2822 | 4.544 15.3% p = .2584 |
| Men Test Site 1 % red. and sig. | 5.083 n = 9 | 4.461 12.2% p = .0513 | 4.100 19.3% p = .0275 | 3.394 33.2% p = .0046 | 3.656 28.1% p = .0351 | 3.394 33.2% p = .0056 |
| Women Test Site 2 % red. and sig. | 4.865 n = 20 | 4.280 12.0% p = .0162 | 3.720 23.5% p = .0045 | 3.630 25.4% p = .0075 | 3.410 29.9% p = .0026 | 3.225 33.7% p = .0083 |
| Women Test Site 1 % red. and sig. | 4.700 n = 22 | 4.095 12.9% p = .0083 | 3.673 21.9% p < .0001 | 2.861 39.1% p < .0001 | 2.286 51.4% p < .0001 | 1.552 67.0% p < .0001 |

FIG. 8B

FOOTWEAR INSOLE FOR ALLEVIATING ARTHRITIS PAIN

FIELD OF THE INVENTION

The present invention relates to footwear insoles to relieve arthritis pain, methods for manufacturing the insoles, and methods for relieving arthritis using the insoles.

BACKGROUND

Footwear insoles are generally inserted into shoes, in order to provide added cushioning or support for the wearer of the shoes. The insoles may be removable and reusable, and they may be one-size-fits-all, specified shoe sizes, or custom-sized to the wearer.

Some insoles offer additional cushioning by providing one or more cushioning layers to the soles of the wearer's shoes. These insoles are generally used to decrease the impact felt by the wearer during walking, jogging, running, or other activities.

For example, U.S. Pat. Nos. 5,068,983 and 5,146,698 describe a combination of foam materials for a resilient base piece, a heel piece, and a top cushioning layer to absorb shock and impact.

Other insoles offer additional foot support by providing a rigid, formed layer placed on top of the soles of the wearer's shoes. These insoles are generally provided to correct abnormal conditions of a wearer's feet or gait.

For example, U.S. Pat. Nos. 6,125,557; 6,269,555; 6,601,320; and 7,124,518 describe a two-piece orthotic assembly having a post member and a plate member for positioning and controlling motions of a wearer's foot in a shoe. U.S. Pat. No. 4,317,293 describes an insole of resiliently elastic material and a stiffening insert at the outside of the foot to ensure a natural position when standing and a natural rolling motion when walking. U.S. Pat. No. 6,502,330 describes a sole strengthener for stabilizing lateral movement of the foot and guiding longitudinal movement of the foot. U.S. Pat. No. 6,732,456 describes an orthotic having a built-in step indicating device (ball) to correct excessive pronation and supination of the foot. U.S. Pat. No. 6,745,501 describes an orthotic having a rigid cap member to correct an abnormal toe-off phase of a gait cycle and prevent shuffling of the toe-off phase by tilting the foot forward via a transverse ridge portion on the underside of the rigid cap member.

Still other insoles provide additional support to specific areas of the foot. For example, U.S. Patent Application No. 2008/0072461 describes an orthotic having a cushioning layer and an outer shell layer, which may optionally include an inner shell insert layer for arch support. In addition, U.S. Patent Application No. 2007/0289170 describes an orthotic having a cushioning layer and a shell layer with a removable insert for arch support. U.S. Pat. Nos. 6,233,847 and 6,618,960 describe a thin, rigid, resiliently flexible cap under a soft, cushioning foam blank to provide proper support to heel and rearfoot areas. U.S. Patent Application Nos. 2002/0050080; 2003/0009915; 2007/0277400; and 2008/0010861 generally describe orthotics for providing support to various areas of the foot.

Some insoles have been proposed to relieve pain in the wearer's knees from medial knee osteoarthritis, with varying results. In this regard, several studies have been conducted to try to confirm the alleviation of knee osteoarthritis by the use of laterally-wedged foot orthotics. For example, in a study by D. Casey Kerrigan et al. described in *Effectiveness of a Lateral-Wedge Insole on Knee Varus Torque in Patients with Knee Osteoarthritis*, ARCH PHYS MED REHABIL, Vol. 83, pp. 889-893 (July 2002), knee varus torque in medial knee osteoarthritis was reduced by using rubber-like foam, lateral-wedge insoles. However, in another study by Kristin Baker et al. described in *A Randomized Crossover Trial of a Wedged Insole for Treatment of Knee Osteoarthritis*, ARTHRITIS & RHEUMATISM, Vol. 56, No. 4, pp. 1198-1203 (April 2007), no statistically significant or clinically important pain relief in medial knee osteoarthritis was found by using incompressible, laterally-wedged foot orthotics.

Further, specifically for alleviating foot arthritis pain, U.S. Pat. Nos. 7,284,342; 6,481,120; and 5,611,153 describe insoles for alleviating foot arthritic problems by using insoles with cushioning layers and pressure redistribution layers. In addition, the American Academy of Orthopaedic Surgeons suggests a soft arch support with a rigid heel for alleviating foot arthritis pain (http://orthoinfo.aaos.org/topic.cfm?topic=A00163).

SUMMARY

There has been a long-felt need for alleviating arthritis pain of the foot, knee, and/or hip. Accordingly, a footwear insole for alleviating arthritis pain of the foot, knee, and/or hip has been created which provides arch support and cushioning for remaining portions of the foot, particularly the heel. Not to be held to any particular theory, it is believed that the combination of arch support and cushioning of the heel alleviates arthritis pain of the foot, knee, and/or hip.

In a non-limiting embodiment of the present invention, an insole for alleviating arthritis pain of at least one of a foot, knee, and hip is provided, comprising a heel portion, an arch portion, and a forefoot portion; the heel portion comprising an interior heel portion and a perimeter heel portion; the arch portion comprising an interior arch portion and a perimeter arch portion; and an upper cushioning layer, a lower cushioning layer, and a rigid shell layer therebetween, the rigid shell layer spanning the heel region and arch region, wherein the rigid shell layer includes an upper surface of the rigid shell layer, a lower surface of the rigid shell layer, and a shell aperture, wherein the shell aperture extends forward from a calcaneus to metatarsals in a medial arch region such that the shell layer provides support along the perimeter heel region and perimeter arch region and the aperture allows for cushioning of the interior heel region and interior arch region; the upper cushioning layer is adhered in part to the upper surface of the rigid shell layer; the lower cushioning layer is adhered in part to the lower surface of the rigid shell layer; the lower cushioning layer includes an arch support region, a heel support region, a forefoot support region, and a lower layer aperture under the calcaneus of the foot; and a portion of the upper cushioning layer extends through a portion of the shell aperture and extends through a portion of the lower layer aperture.

In an alternative non-limiting embodiment of the invention, the rigid shell layer is configured to support the metatarsals in the medial arch region of the foot.

In an alternative non-limiting embodiment of the invention, the insole has a topcloth adhered to an upper surface of the upper cushioning layer.

In an alternative non-limiting embodiment of the invention, the topcloth is polyester.

In an alternative non-limiting embodiment of the invention, the upper cushioning layer and the lower cushioning layer are polyurethane foam.

In an alternative non-limiting embodiment of the invention, the rigid shell layer is polypropylene.

In an alternative non-limiting embodiment of the invention, the topcloth and the upper cushioning layer are coterminous in lateral and longitudinal dimensions.

In an alternative non-limiting embodiment of the invention, the longitudinal dimensions of the topcloth and the upper cushioning layer extend approximately from the calcaneus to the metatarsals of the foot.

In an alternative non-limiting embodiment of the invention, the lower cushioning layer has a longitudinal dimension less than a shorter of a longitudinal dimension of the topcloth and a longitudinal dimension of the upper cushioning layer.

In an alternative non-limiting embodiment of the invention, the rigid shell layer has a longitudinal dimension less than a shorter of a longitudinal dimension of the topcloth, the upper cushioning layer, and the lower cushioning layer.

In an alternative non-limiting embodiment of the invention, the upper cushioning layer completely covers the upper surface of the rigid shell layer, and the lower cushioning layer completely covers the lower surface of the rigid shell layer.

In an alternative non-limiting embodiment of the invention, the lower cushioning layer has a varying thickness.

In an alternative non-limiting embodiment of the invention, the arch support region has greater thickness than at least one of the heel support region and the toe support region.

In an alternative non-limiting embodiment of the invention, at least one of the rigid shell layer, the lower cushioning layer, and the upper cushioning layer is contoured to provide arch support.

In an alternative non-limiting embodiment of the invention, at least one of the rigid shell layer, the lower cushioning layer, and the upper cushioning layer is contoured to provide heel support.

In an alternative non-limiting embodiment of the invention, the heel support is a heel cup.

In an alternative non-limiting embodiment of the invention, a lower surface of the upper cushioning layer is contoured to receive the upper surface of the rigid shell layer.

In an alternative non-limiting embodiment of the invention, the upper cushioning layer, the rigid shell layer, and the lower cushioning layer are adhered together, and wherein the portion of the upper cushioning layer extending through the shell aperture and the lower layer aperture is mated with the lower cushioning layer.

In an alternative non-limiting embodiment of the invention, the rigid shell layer provides support for at least one of a first metatarsal and a second metatarsal of the foot.

In an alternative non-limiting embodiment of the invention, the lower cushioning layer is configured to contact an inner sole of a shoe.

In an alternative non-limiting embodiment of the invention, the insole is a removable device for insertion in footwear.

In an alternative non-limiting embodiment of the invention, the insole is integrated in a footwear device.

In another non-limiting embodiment of the present invention, a method of assembling an insole for alleviating arthritis pain of at least one of a foot, knee, and hip is provided, comprising the step of adhering an upper cushioning layer, a lower cushioning layer, and a rigid shell layer therebetween; wherein the rigid shell layer is located in an area below the foot between a calcaneus and metatarsals of the foot for providing arch support, such that the rigid shell layer supports the metatarsals in a medial arch region; the rigid shell layer includes a shell aperture under the calcaneus of the foot, the shell aperture extends forward from the calcaneus to the metatarsals in the medial arch region; and a portion of the upper cushioning layer extends through the shell aperture.

In an alternative non-limiting embodiment of the invention, the lower cushioning layer includes a lower layer aperture under the calcaneus of the foot; and the portion of the upper cushioning layer extending through the shell aperture extends through the lower layer aperture.

In an alternative non-limiting embodiment of the invention, the method further comprises the step of adhering a topcloth to the upper cushioning layer.

In another non-limiting embodiment of the present invention, an insole for alleviating arthritis pain of at least one of a foot, knee, and hip in a subject is provided, comprising a cushioning element and a support element, the support element comprising rigid material containing an aperture, such that the support element provides support along a perimeter of a heel region and a perimeter of an arch region of the foot and the aperture allows for cushioning of an interior heel region and an interior arch region by the cushioning element.

In an alternative non-limiting embodiment of the invention, the cushioning element comprises polyurethane foam.

In an alternative non-limiting embodiment of the invention, the support element comprises polypropylene.

In another non-limiting embodiment of the present invention, a method of alleviating arthritis pain of at least one of a foot, knee, and hip in a subject is provided, comprising contacting the foot with an insole comprising a cushioning element and a support element, the support element comprising rigid material containing an aperture, such that the support element provides support along a perimeter of a heel region and a perimeter of an arch region of the foot and the aperture allows for cushioning of an interior heel region and an interior arch region by the cushioning element.

In an alternative non-limiting embodiment of the invention, when the insole is in use, the support element is positioned in an area below the foot between a calcaneus and metatarsals of the foot, such that the support element supports the metatarsals in a medial arch region, and the aperture is positioned under the calcaneus of the foot and extends forward from the calcaneus to the metatarsals in the medial arch region of the foot.

In an alternative non-limiting embodiment of the invention, the insole is a removable device for insertion in footwear.

In an alternative non-limiting embodiment of the invention, the insole is integrated in a footwear device.

In yet another non-limiting embodiment of the present invention, a method of alleviating arthritis pain of at least one of a foot, knee, and hip with an insole of a shoe of a person having arthritis pain is provided, comprising the steps of providing cushioning by a topcloth, an upper cushioning layer, and a lower cushioning layer of the insole; and providing support by a rigid shell layer located between the upper cushioning layer and the lower cushioning layer of the insole in an area below the foot between a calcaneus and metatarsals of the foot, such that the rigid shell layer extends forward under the metatarsals in a medial arch region; wherein the rigid shell layer includes a shell aperture under the calcaneus of the foot, the shell aperture extends forward from the calcaneus to the metatarsals in the medial arch region; the lower cushioning layer includes a lower layer aperture under the calcaneus of the foot; and a portion of the upper cushioning layer extends through the shell aperture and extends through the lower layer aperture.

In an alternative non-limiting embodiment of the invention, the method further comprises the step of inserting the insole into the shoe of the person having arthritis pain, wherein the combination of support of the shell layer and cushioning of the topcloth, upper cushioning layer, and lower cushioning layer provides for arthritis pain relief.

Other features and aspects of the present invention will become more fully apparent from the following brief description of the drawings, the detailed description of the non-limiting embodiments, the appended claims and the accompanying drawings.

BRIEF DESCRIPTION OF THE DRAWINGS

FIG. 1A is a medial side view of an embodiment of an exemplary footwear insole, in accordance with the present invention.

FIG. 1B is a top view of the embodiment of the exemplary footwear insole, in accordance with the present invention.

FIG. 1C is a lateral side view of the embodiment of the exemplary footwear insole, in accordance with the present invention.

FIG. 1D is a bottom view of the embodiment of the exemplary footwear insole, in accordance with the present invention.

FIG. 1E is a rear view of the embodiment of the exemplary footwear insole, in accordance with the present invention.

FIG. 2A is a longitudinal cross-sectional view, along line A-A' shown in FIG. 1B of the embodiment of the exemplary footwear insole, in accordance with the present invention.

FIG. 2B is a lateral cross-sectional view, along line B-B' shown in FIG. 2A, of the embodiment of the exemplary footwear insole, in accordance with the present invention.

FIG. 2C is a lateral cross-sectional view, along line C-C' shown in FIG. 2A, of the embodiment of the exemplary footwear insole, in accordance with the present invention.

FIG. 2D is a lateral cross-sectional view, along line D-D' shown in FIG. 2A, of the embodiment of the exemplary footwear insole, in accordance with the present invention.

FIG. 2E is a lateral cross-sectional view, along line E-E' shown in FIG. 2A, of the embodiment of the exemplary footwear insole, in accordance with the present invention.

FIG. 3A is a top plan view of a rigid shell layer of the embodiment of the exemplary footwear insole, in accordance with the present invention.

FIG. 3B is a medial side view of the rigid shell layer of the embodiment of the exemplary footwear insole, in accordance with the present invention.

FIG. 3C is a longitudinal cross-sectional view, along line F-F' shown in FIG. 3A, of the rigid shell layer of the embodiment of the exemplary footwear insole, in accordance with the present invention.

FIG. 3D is a substantially longitudinal cross-sectional view, along line G-G' shown in FIG. 3A, of the rigid shell layer of the embodiment of the exemplary footwear insole, in accordance with the present invention.

FIG. 3E is a longitudinal cross-sectional view, along line H-H' shown in FIG. 3A, of the rigid shell layer of the embodiment of the exemplary footwear insole, in accordance with the present invention.

FIG. 3F is a schematic bottom view of a foot, in which the bones of the foot are representatively shown.

FIG. 3G is a bottom plan view of the rigid shell layer of the embodiment of the exemplary footwear insole, in accordance with the present invention, wherein the rigid shell layer is shown superimposed upon the schematic bottom view of the foot of FIG. 3F.

FIG. 5 is a table of arthritis pain test subjects, broken down by arthritis site and testing site.

FIG. 6A is a table of the test results for subjects having arthritis pain in the knee.

FIG. 6B is a table of the test results for subjects having arthritis pain in the knee, broken down by testing site.

FIG. 7A is a table of the test results for subjects having arthritis pain in the foot.

FIG. 7B is a table of the test results for subjects having arthritis pain in the foot, broken down by testing site.

FIG. 8A is a table of the test results for subjects having arthritis pain in the hip.

FIG. 8B is a table of the test results for subjects having arthritis pain in the hip, broken down by testing site.

DETAILED DESCRIPTION OF THE EMBODIMENTS

Figure 4:
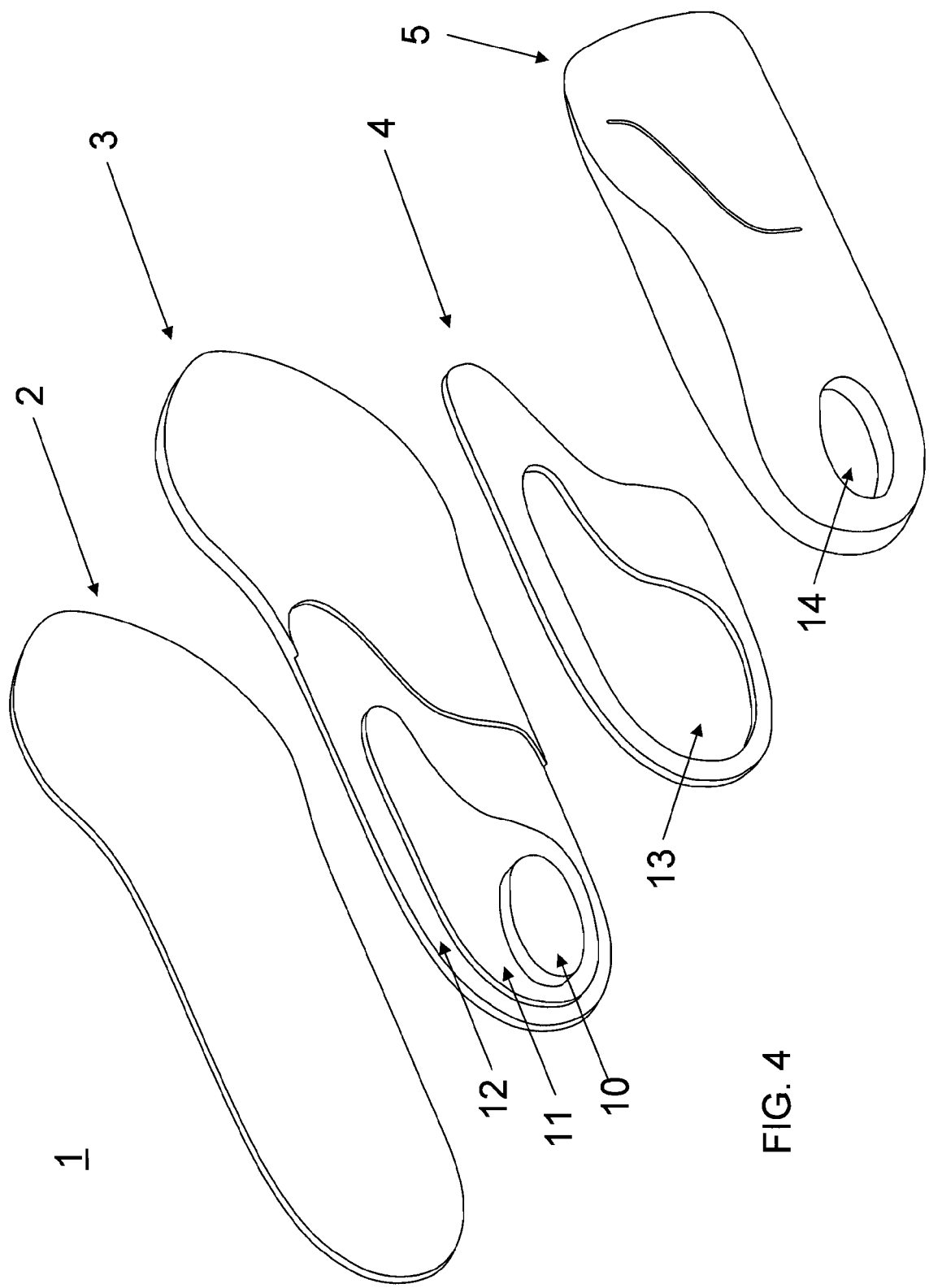
FIG. 4 is an exploded perspective, bottom view of the embodiment of the exemplary footwear insole, illustrating a topcloth 2, an upper cushioning layer 3, a rigid shell layer 4, and a lower cushioning layer 5, in accordance with the present invention.

The Figures depict an embodiment of an exemplary footwear insole 1, in accordance with the present invention. Although the Figures show a left-footed embodiment of the exemplary footwear insole, it is to be understood that a right-footed embodiment of the exemplary footwear insole would be a mirror image of the Figures shown.

FIGS. 1A to 1E show different views of an embodiment of an exemplary footwear insole 1. FIG. 1A is a medial side view, FIG. 1B is a top view, FIG. 1C is a lateral side view, FIG. 1D is a bottom view, and FIG. 1E is a rear view of the embodiment of the exemplary footwear insole 1. FIGS. 1A, 1B, 1C, and 1E show a topcloth 2 forming a top layer of the insole 1. As shown, the topcloth 2 may cover the entire insole longitudinally from the toe region 6 to the heel region 9, and laterally from the lateral arch region 8 to the medial arch region 7, such that in a top view (FIG. 1B), only the topcloth 2 is visible. However, the topcloth 2 may alternatively cover only a portion of the top of the footwear insole 1, such that an upper cushioning layer 3 below the topcloth 2 may be visible in a top view. In addition, the topcloth 2 may or may not extend to an area under the toes. The topcloth 2 may be made of a fabric, a polymer, a natural fiber, a film, or any other material to provide a comfortable mating surface for a user's foot. For example, the topcloth 2 may be made of polyester, acetate, polyethene, acrylic, nylon, rayon, spandex, wool, cotton, silk, bamboo, linen, hemp, urethane, polyethylene, polyurethane, or any other material that may provide a comfortable mating surface.

FIGS. 1A, 1C, 1D, and 1E also show an upper cushioning layer 3 positioned below the topcloth 2. As shown, the upper cushioning layer 3 is coterminous in lateral and longitudinal dimensions with the topcloth 2. As discussed above, although the topcloth 2 may alternatively cover only a portion of a top surface of the upper cushioning layer 3, leaving a portion of the top surface of the upper cushioning layer 3 exposed to a user's foot, the topcloth 2 generally will not have a larger lateral or longitudinal dimension than the upper cushioning layer 3. In addition, as shown in FIG. 1D, the upper cushioning layer 3 may include a heel cushioning pad 10 in the heel region 9, positioned under a calcaneus 16 of a user's foot 15. Further, the upper cushioning layer 3 may be provided with a curvature on its upper surface in order to comfortably fit the contours of a user's foot. The upper cushioning layer 3 may be made of a foam, a gel, or any other cushioning material. For example, the upper cushioning layer 3 may be made of polyurethane, ethylene vinyl acetate copolymer, styrene-ethylene-butadiene-styrene, silicone, hydrogel, or any other cushioning material.

FIGS. 1A, 1C, 1D, and 1E also show a rigid shell layer 4 positioned below the upper cushioning layer 3. The rigid shell layer 4 may generally have a longitudinal dimension shorter than the longitudinal dimension of the upper cushioning layer 3, and the rigid shell layer 4 may have a lateral dimension equal to or shorter than the lateral dimension of the upper cushioning layer 3, such that the rigid shell layer 4 does not directly contact a user's foot. Further, as shown in FIGS. 1A and 1C, the rigid shell layer 4 may be shaped to have a longer longitudinal dimension in the medial arch region 7 than in the lateral arch region 8. In this manner, the rigid shell layer 4 may provide greater support for the medial arch region 7, than for the lateral arch region 8, of the user's foot. In addition, the rigid shell layer 4 may be provided with a curvature in order to comfortably fit the contours of a user's foot. The rigid shell layer 4 may be made of any rigid, semi-flexible material which can provide support to a user's foot while also providing a comfortable fit. Such materials include, but are not limited to, polymer materials such as polyolefins, polyamides, polyesters, polyurethanes, styrenic elastomers, and polycarbonates. All of the aforementioned materials can be filled with glass, mineral or carbon fibers.

FIGS. 1A, 1C, 1D, and 1E also show a lower cushioning layer 5 positioned below the rigid shell layer 4. The lower cushioning layer 5 may generally have a longitudinal dimension shorter than the longitudinal dimension of the upper cushioning layer 3, and a lateral dimension approximately equal to the lateral dimension of the upper cushioning layer 3. Further, the lower cushioning layer 5 may generally have a longitudinal dimension longer than the longitudinal dimension of the rigid shell layer 4, and a lateral dimension equal to or greater than the lateral dimension of the rigid shell layer 4, such that the rigid shell layer 4 does not directly contact a sole of a user's shoe. Similar to the rigid shell layer 4, an upper surface of the lower cushioning layer 5 may be provided with a curvature in order to comfortably fit the contours of a user's foot. In addition, as shown in FIGS. 1D and 1E, a lower surface and sidewalls of the lower cushioning layer 5 may be contoured or tapered, particularly in the medial arch region 7, heel region 9, and lateral arch region 8, in order to better fit within a user's shoe. Further, as shown in FIG. 1D, the lower cushioning layer 5 may include a lower layer aperture 14 in the heel region 9, positioned under a calcaneus 16 of a user's foot 15, and through which the heel cushioning pad 10 of the upper cushioning layer 3 extends. Similar to the upper cushioning layer 3, the lower cushioning layer 5 may be made of a foam, a gel, or any other cushioning material. For example, the lower cushioning layer 5 may be made of polyurethane, ethylene vinyl acetate copolymer, styrene-ethylene-butadiene-styrene, silicone, hydrogel, or any other cushioning material. The upper cushioning layer and the lower cushioning layer may be constructed of the same or different materials.

FIG. 2A shows a longitudinal cross-sectional view, along line A-A' shown in FIG. 1B, of the embodiment of the exemplary footwear insole 1. As described above, the topcloth 2 may cover an entire top surface of the insole. Positioned below the topcloth 2, the upper cushioning layer 3 spans the entire longitudinal dimension of the insole. Positioned below the upper cushioning layer 3, the rigid shell layer 4 is received in a lower surface of the upper cushioning layer 3. Positioned below the rigid shell layer 4 is the lower cushioning layer 5. In particular, the heel cushioning pad 10 of the upper cushioning layer 3 under the calcaneus 16 of the user's foot 15 extends from a lower surface of the topcloth 2 through both a shell aperture 13 in the rigid shell layer 4 and a lower layer aperture 14 in the lower cushioning layer 5 to a lower surface that is substantially flush with a lower surface of the lower cushioning layer 5. As shown, the upper cushioning layer 3, the rigid shell layer 4, and the lower cushioning layer 5 may be provided with a longitudinal curvature in order to comfortably fit the contours of a user's foot. In particular, as shown in FIG. 2A, the longitudinal curvature of the upper cushioning layer 3, the rigid shell layer 4, and the lower cushioning layer 5 may provide a thinner cross-section in the toe region 6, a thicker cross-section in the medial and lateral arch regions 7, 8, and/or a heel cup in the heel region 9.

FIG. 2B shows a lateral cross-sectional view, along line B-B' shown in FIG. 2A, of the embodiment of the exemplary footwear insole 1. This cross-section of the insole may include the topcloth 2 and the upper cushioning layer 3. In addition, this cross-section of the insole may include only the upper cushioning layer 3. The lateral width of the insole in this cross-section may be sized to be approximately equal to the width of a user's foot, in order to comfortably fit within a user's shoe.

FIG. 2C shows a lateral cross-sectional view, along line C-C' shown in FIG. 2A, of the embodiment of the exemplary footwear insole 1. This cross-section of the insole may include the topcloth 2, the upper cushioning layer 3, and the lower cushioning layer 5. The lower cushioning layer 5 may be provided with a curvature on its top surface in order to comfortably fit the contours of a user's foot. In particular, as shown in FIG. 2C, the lower cushioning layer 5 may provide a thicker cross-section in the medial arch region 7 and a relatively thinner cross-section in the lateral arch region 8. The lateral width of the insole in this cross-section may be sized to be approximately equal to the width of a user's foot, and the sidewalls of the lower cushioning layer 5 may be contoured or tapered, particularly in the medial arch region 7 and lateral arch region 8, in order to better fit within a user's shoe.

FIG. 2D shows a lateral cross-sectional view, along line D-D' shown in FIG. 2A, of the embodiment of the exemplary footwear insole 1. This cross-section of the insole may include the topcloth 2, the upper cushioning layer 3, the rigid shell layer 4, and the lower cushioning layer 5. As shown, the rigid shell layer 4 may be received in a lower surface of the upper cushioning layer 3. Further, the rigid shell layer 4 may be shaped in order to provide greater support for the medial arch region 7, than for the lateral arch region 8, of the user's foot. In addition, the lower cushioning layer 5 may be provided with a curvature on its top surface in order to comfortably fit the contours of a user's foot. In particular, as shown in FIG. 2D, the rigid shell layer 4 and the lower cushioning layer 5 may provide stiffer support in the medial arch region 7 than in the lateral arch region 8. The lateral width of the insole in this cross-section may be sized to be approximately equal to the width of a user's foot, and a lower surface and sidewalls of the lower cushioning layer 5 may be contoured or tapered, particularly in the medial arch region 7 and lateral arch region 8, in order to better fit within a user's shoe.

FIG. 2E shows a lateral cross-sectional view, along line E-E' shown in FIG. 2A, of the embodiment of the exemplary footwear insole 1. This cross-section of the insole may include the topcloth 2, the upper cushioning layer 3, the rigid shell layer 4, and the lower cushioning layer 5. As shown, the rigid shell layer 4 may be received in a lower surface of the upper cushioning layer 3. Further, the rigid shell layer 4 may include a shell aperture 13 in the heel region 9, positioned under a calcaneus 16 of a user's foot 15. In addition, the lower cushioning layer 5 may include a lower layer aperture 14 in the heel region 9, positioned under the calcaneus 16 of the user's foot 15. Moreover, the upper cushioning layer 3 may include a heel cushioning pad 10 in the heel region 9, positioned under the calcaneus 16 of the user's foot 15. The heel cushioning pad 10 may extend through both the shell aperture 13 and the lower layer aperture 14 to a lower surface that is substantially flush with a lower surface of the lower cushioning layer 5. Optionally, the heel cushioning pad 10 and the lower surface 11 (shown in FIG. 4) of the upper cushioning layer 3 may be separate layers of cushioning material. Further optionally, the lower cushioning layer 5, instead of the upper cushioning layer 3, may include the heel cushioning pad 10 in the heel region 9 (not shown); then, the heel cushioning pad 10 of the lower cushioning layer 5 may extend through the shell aperture 13 and abut the lower surface 11 of the upper cushioning layer 3, or the heel cushioning pad 10 may extend through the shell aperture 13 to mate with an upper layer aperture (not shown) of the upper cushioning layer 3. In addition, the upper cushioning layer 3, the rigid shell layer 4, and the lower cushioning layer 5 may be provided with a curvature in order to comfortably fit the contours of a user's foot. In particular, as shown in FIG. 2E, the curvature of the upper cushioning layer 3, the rigid shell layer 4, and the lower cushioning layer 5 may provide a heel cup in the heel region 9 with support around the periphery of the heel region 9. The lateral width of the insole in this cross-section may be sized to be approximately equal to the width of a user's foot, and a lower surface and sidewalls of the lower cushioning layer 5 may be contoured or tapered, particularly in the heel region 9, in order to better fit within a user's shoe.

FIG. 3A shows a top plan view of a rigid shell layer 4 of the embodiment of the exemplary footwear insole 1. As shown, the rigid shell layer 4 may be shaped to have a longer longitudinal dimension in the medial arch region 7 than in the lateral arch region 8. Further, the shell aperture 13 may also be shaped to have a longer longitudinal dimension in the medial arch region 7 than in the lateral arch region 8. In this manner, the support provided by the rigid shell layer 4 may be further localized to the medial arch region 7, while still providing a level of support to the lateral arch region 8 and around a periphery of the heel region 9. The particular shape of the rigid shell layer 4 and the shell aperture 13 is further described below.

FIG. 3B shows a medial side view, FIG. 3C shows a longitudinal cross-sectional view, along line F-F', shown in FIG. 3A, FIG. 3D shows a substantially longitudinal cross-sectional view, along line G-G', shown in FIG. 3A, and FIG. 3E shows a longitudinal cross-sectional view, along line H-H', shown in FIG. 3A, of the rigid shell layer 4 of the embodiment of the exemplary footwear insole 1. As shown, the rigid shell layer 4 may be provided with a longitudinal curvature in order to comfortably fit the contours of a user's foot. In particular, the rigid shell layer 4 may be contoured to provide a heel cup in the heel region 9, stiffer support in the medial and lateral arch regions 7, 8, and/or relatively less support in the toe region 6 and around the periphery of the heel region 9. The rigid shell layer 4 may be made of any rigid, semi-flexible material which can provide support to a user's foot while also providing a comfortable fit.

FIG. 3F shows a schematic bottom view of a foot 15, in which the bones of the foot 15 are representatively shown. The calcaneus 16 is shown in the heel region 9 of the foot 15. Spanning the foot from the medial arch region 7 to the lateral arch region 8 are the first metatarsal bone 17, second metatarsal bone 18, third metatarsal bone 19, fourth metatarsal bone 20, and fifth metatarsal bone 21. Connected to the metatarsal bones 17 to 21 toward the calcaneus 16 are the medial cuneiform bone 23, intermediate cuneiform bone 24, lateral cuneiform bone 25, and cuboid 26.

FIG. 3G shows a bottom plan view of the rigid shell layer 4, wherein the rigid shell layer is shown superimposed upon the schematic bottom view of the foot 15 of FIG. 3F. The rigid shell layer 4 may be shaped to have a longer longitudinal dimension in the medial arch region 7 than in the lateral arch region 8. Specifically, the outer peripheral edge of the rigid shell layer 4 in the heel region 9 may substantially follow the outer edge of the foot 15 in the heel region 9. Forward of the heel region 9 and in the medial arch region 7, the outer peripheral edge of the rigid shell layer 4 may continue to follow the outer edge of the foot 15 until reaching approximately the metatarsal-phalangeal joint 22 of the first metatarsal 17. Then, the outer peripheral edge of the rigid shell layer 4 may follow a curve approximately under the metatarsal-phalangeal joint 22 of the first metatarsal 17. The outer peripheral edge of the rigid shell layer 4 may then follow a curve approximately under the second metatarsal 18 away from the metatarsal-phalangeal joints 22 and toward the tarsal-metatarsal joints 27 of the foot 15. Then, still forward of the heel region 9 and in the lateral arch region 8, the outer peripheral edge of the rigid shell layer 4 may follow a curve approximately under the tarsal-metatarsal joints 27 of the third, fourth, and fifth metatarsals 19, 20, 21. Thereafter, the outer peripheral edge of the rigid shell layer 4 may follow the outer edge of the foot 15 as it continues rearward to and around the heel region 9. In this manner, by extending forward in the medial arch region 7 but not in the lateral arch region 8, the rigid shell layer 4 may provide greater support for the medial arch region 7, than for the lateral arch region 8, of the user's foot 15.

Further, as shown in FIG. 3G, the shell aperture 13 may also be shaped to have a longer longitudinal dimension in the medial arch region 7 than in the lateral arch region 8, creating a shell aperture 13 roughly similar in shape to the outer peripheral edge of the rigid shell layer 4. Specifically, the edge of the shell aperture 13 in the heel region 9 may substantially follow the outer peripheral edge of the rigid shell layer 4 in the heel region 9, separated from the outer peripheral edge of the rigid shell layer 4 by a short distance toward the center of the heel region 9. Forward of the heel region 9 and in the medial arch region 7, the edge of the shell aperture 13 may continue to follow the outer peripheral edge of the rigid shell layer 4 separated by a short distance toward the center of the foot 15 until reaching approximately the tarsal-metatarsal joint 27 of the first metatarsal 17. Then, the edge of the shell aperture 13 may follow a curve approximately under the tarsal-metatarsal joints 27 of the first and second metatarsals 17, 18. Then, the edge of the shell aperture 13 may follow a curve approximately under the intermediate and lateral cuneiform bones 24, 25 away from the tarsal-metatarsal joints 27 and toward the heel region 9 of the foot 15. Then, still forward of the heel region 9 and in the lateral arch region 8, the edge of the shell aperture 13 may follow a curve approximately under the cuboid bone 26. Thereafter, the edge of the shell aperture 13 may follow the outer peripheral edge of the rigid shell layer 4 as it continues rearward to and around the heel region 9, separated from the outer peripheral edge of the rigid shell layer 4 by a short distance toward the center of the heel region 9. In this manner, the support provided by the rigid shell layer 4 may be further localized to the medial arch region 7, while still providing a level of support to the lateral arch region 8 and around a periphery of the heel region 9.

FIG. 4 shows an exploded perspective, bottom view of the embodiment of the exemplary footwear insole 1, illustrating a topcloth 2, an upper cushioning layer 3, a rigid shell layer 4, and a lower cushioning layer 5. The topcloth 2 may cover the entire insole longitudinally from the toe region 6 to the heel region 9, and laterally from the lateral arch region 8 to the medial arch region 7. In addition, the topcloth 2 may have a substantially uniform thickness. Further, the topcloth 2 may be made of a fabric, a polymer, a natural fiber, a film, or any other material to provide a comfortable mating surface for a user's foot.

As shown in FIG. 4, the upper cushioning layer 3 may cover the entire insole longitudinally from the toe region 6 to the heel region 9, and laterally from the lateral arch region 8 to the medial arch region 7. In addition, upper cushioning layer 3 may include a receiving surface 12 on its lower surface, which receiving surface 12 receives the rigid shell layer 4. The upper cushioning layer 3 also may include a heel cushioning pad 10 in the heel region 9, positioned under a calcaneus 16 of a user's foot 15. Moreover, the upper cushioning layer 3 may be provided with a curvature in order to comfortably fit the contours of a user's foot. Further, the upper cushioning layer 3 may be made of a foam, a gel, or any other cushioning material.

As shown in FIG. 4, the rigid shell layer 4 may be received in a receiving surface 12 of the upper cushioning layer 3. Further, the rigid shell layer 4 may include a shell aperture 13 shaped to provide support in the medial arch region 7 of a user's foot, and positioned under a calcaneus 16 of a user's foot 15. Once received in the receiving surface 12 of the upper cushioning layer 3, a lower surface of the rigid shell layer 4 may be substantially flush with both a lower surface of the upper cushioning layer 3 in the toe region 6 and also a lower surface 11 of the upper cushioning layer 3 in the heel region 9. In addition, the heel cushioning pad 10 of the upper cushioning layer 3 may extend through the shell aperture 13 of the rigid shell layer 4. Moreover, the rigid shell layer 4 may be provided with a curvature in order to comfortably fit the contours of a user's foot. The rigid shell layer 4 may be made of any rigid, semi-flexible material which can provide support to a user's foot while also providing a comfortable fit.

As shown in FIG. 4, the lower cushioning layer 5 may have a longitudinal dimension shorter than the longitudinal dimension of the upper cushioning layer 3 but longer than the longitudinal dimension of the rigid shell layer 4, and a lateral dimension approximately equal to the lateral dimensions of the upper cushioning layer 3 and the rigid shell layer 4, such that the rigid shell layer 4 does not directly contact a sole of a user's shoe. The lower cushioning layer 5 may include a lower layer aperture 14, positioned under a calcaneus 16 of a user's foot 15. The heel cushioning pad 10 of the upper cushioning layer 3 may extend through the lower layer aperture 14 of the lower cushioning layer 5, such that a lower surface of the heel cushioning pad 10 may be substantially flush with a lower surface of the lower cushioning layer 5. Further, similar to the rigid shell layer 4, an upper surface of the lower cushioning layer 5 may be provided with a curvature in order to comfortably fit the contours of a user's foot. In addition, the lower surface and sidewalls of the lower cushioning layer 5 may be contoured or tapered, particularly in the medial arch region 7, heel region 9, and lateral arch region 8, in order to better fit within a user's shoe. Similar to the upper cushioning layer 3, the lower cushioning layer 5 may be made of a foam, a gel, or any other cushioning material.

The topcloth 2, the upper cushioning layer 3, the rigid shell layer 4, and the lower cushioning layer 5 may be adhered together by an adhesive or tape. Any appropriate adhesive or tape, which adheres the materials of the different layers together and maintains adhesion under conditions of use of the insole, such as walking, running, jumping, or any other activity, may be used. In alternative acceptable embodiments, adhesion of the layers can be accomplished by pressure sensitive adhesives, solvent based adhesives, hot melt adhesives, radio frequency welding, ultrasonically welding or combinations thereof.

The rigid shell layer 4 may provide rigid support for a user's foot, which may be further localized to the medial arch region 7 by the shape of the rigid shell layer 4 and the shell aperture 13. This rigid support in the medial arch region 7 may provide support to and prevent collapse of the bones in the medial arch of a user's foot 15, thereby alleviating arthritis pain in the medial arch of a user's foot. In addition, the rigid shell layer 4 may also provide a level of rigid support to the lateral arch region 8 and around a periphery of the heel region 9. Further, the rigid shell layer 4 may also include a shell aperture 13, positioned under a calcaneus 16 of a user's foot 15, through which a heel cushioning pad 10 of the upper cushioning layer 3 extends from a lower surface of the topcloth 2 to a lower surface of the insole 1. Moreover, the rigid shell layer 4 is positioned between an upper cushioning layer 3 and a lower cushioning layer 5, thereby providing overall cushioning to all regions of a user's foot. Thus, the topcloth 2, the upper cushioning layer 3, the rigid shell layer 4, and the lower cushioning layer 5 may simultaneously provide both rigid support to the medial arch region 7, with a lower level of support for the lateral arch region 8 and around a periphery of the heel region 9, and also cushioning support for all regions of a user's foot, particularly the heel region 9.

In a preferred non-limiting embodiment of the present invention, the insole 1 may be a ¾ length insole which extends longitudinally forward from the heel region 9 to a position in the toe region 6 approximately underneath the metatarsal bones 17 to 21 of a user's foot 15. The topcloth 2 may preferably be made of 100% polyester, the upper cushioning layer 3 may preferably be made of polyurethane foam, the rigid shell layer 4 may preferably be made of polypropylene, and the lower cushioning layer 5 may preferably be made of polyurethane foam. The topcloth 2, the upper cushioning layer 3, the rigid shell layer 4, and the lower cushioning layer 5 may preferably be adhered using hot melt adhesive. Further, the insole may preferably simultaneously provide localized, rigid arch support in the medial arch region 7 and cushioning support in the heel region 9 under a calcaneus 16 of a user's foot 15.

Although the foregoing description provides a lower cushioning layer 5 with a lower layer aperture 14, a rigid shell layer 4 with a shell aperture 13, and an upper cushioning layer 3 with a heel cushioning pad 10 that extends through the shell aperture 13 and the lower layer aperture 14, it may be possible to modify the construction of the individual elements such that the upper cushioning layer 3 includes an upper layer aperture (not shown), the rigid shell layer 4 includes a shell aperture 13, and the lower cushioning layer 5 includes a heel cushioning pad (not shown) that extends through the upper layer aperture of the upper cushioning layer 3 and through the shell aperture 13 of the rigid shell layer 4.

A method of assembling an insole 1 for alleviating arthritis pain of a foot, knee, and/or hip may comprise the step of adhering an upper cushioning layer 3, a lower cushioning layer 5, and a rigid shell layer 4 therebetween; wherein the rigid shell layer 4 is located in an area below the foot between a calcaneus and metatarsals of the foot for providing arch support, such that the rigid shell layer 4 supports the metatarsals in a medial arch region; wherein the rigid shell layer 4 includes a shell aperture 13 under the calcaneus of the foot, the shell aperture 13 extends forward from the calcaneus to the metatarsals in the medial arch region; and wherein a portion of the upper cushioning layer 3 extends through the shell aperture 13. The method of assembling the insole 1 for alleviating arthritis pain of a foot, knee, and/or hip may further comprise the step of adhering a topcloth 2 to the upper cushioning layer 3. In addition, the lower cushioning layer 5 may include a lower layer aperture 14 under the calcaneus of the foot; and the portion of the upper cushioning layer 3 extending through the shell aperture 13 extends through the lower layer aperture 14.

A method of alleviating arthritis pain of a foot, knee, and/or hip with an insole 1 of a shoe of a person having arthritis pain, may comprise the steps of providing cushioning by a topcloth 2, an upper cushioning layer 3, and a lower cushioning layer 5 of the insole 1; and providing arch support by a rigid shell layer 4 located between the upper cushioning layer 3 and the lower cushioning layer 5 of the insole 1 in an area below the foot between a calcaneus and metatarsals of the foot, such that the rigid shell layer 4 extends forward under the metatarsals in a medial arch region; wherein the rigid shell layer 4 includes a shell aperture 13 under the calcaneus of the foot, the shell aperture 13 extends forward from the calcaneus to the metatarsals in the medial arch region; wherein the lower cushioning layer 5 includes a lower layer aperture 14 under the calcaneus of the foot; and wherein a portion of the upper cushioning layer 3 extends through the shell aperture 13 and extends through the lower layer aperture 14. The method of alleviating arthritis pain of the foot, knee, and/or hip with an insole 1 of a shoe of a person having arthritis pain may further comprise the step of inserting the insole 1 into the shoe of the person having arthritis pain, wherein the combination of support of the arch and cushioning of the heel provides for arthritis pain relief.

Embodiments of the exemplary footwear insole of the present invention were tested for alleviating arthritis pain of the foot, hip, and knee on arthritis pain test subjects. Two hundred and twenty eight test subjects were evaluated, broken down by arthritis site and testing site as shown in FIG. 5. The test subjects were screened based on a number of criteria including, for example, age, general health, body mass index, arthritis site, shoe size, normal daily activities, and others. In addition, for each of the testing sites, the daily environmental conditions including, for example, humidity, barometric pressure, temperature, and weather conditions were tracked and documented.

Reduction in pain was evaluated based on each test subject's self evaluation of intensity of pain on a scale of 1-10, referred to herein as visual analog scale (VAS). For each group of subjects, males and females, and for each arthritis pain site, an initial baseline VAS score was determined. Next the VAS score, the percent reduction in the VAS score compared to the baseline VAS score, and the statistical p-value were evaluated after one minute, eight hours, one week, two weeks, and three weeks of using embodiments of the exemplary footwear insole. Statistical significance for the results was determined at $p \leq 0.05$.

FIG. 6A shows the test results for subjects having arthritis pain in the knee. FIG. 6A includes data points for the baseline VAS scores and VAS scores after one minute, eight hours, one week, two weeks, and three weeks of using embodiments of the exemplary footwear insole. All the data are considered statistically significant based on the above criteria.

FIG. 6B shows the test results for subjects having arthritis pain in the knee, broken down by testing site. Similar to FIG. 6A, for each group of subjects, an initial baseline VAS score was determined. FIG. 6B includes data points for the VAS scores after one minute, eight hours, one week, two weeks, and three weeks of using embodiments of the exemplary footwear insole. As shown, the data for both males and females at test site 1 showed immediate, all day, and sustained pain relief of the arthritis pain in the knee, and this data is considered statistically significant based on the above criteria. In addition, the data for both males and females at test site 2 showed statistically significant reduced VAS scores after eight hours, one week, two weeks, and three weeks as compared to the baseline VAS scores.

Figure 6C:
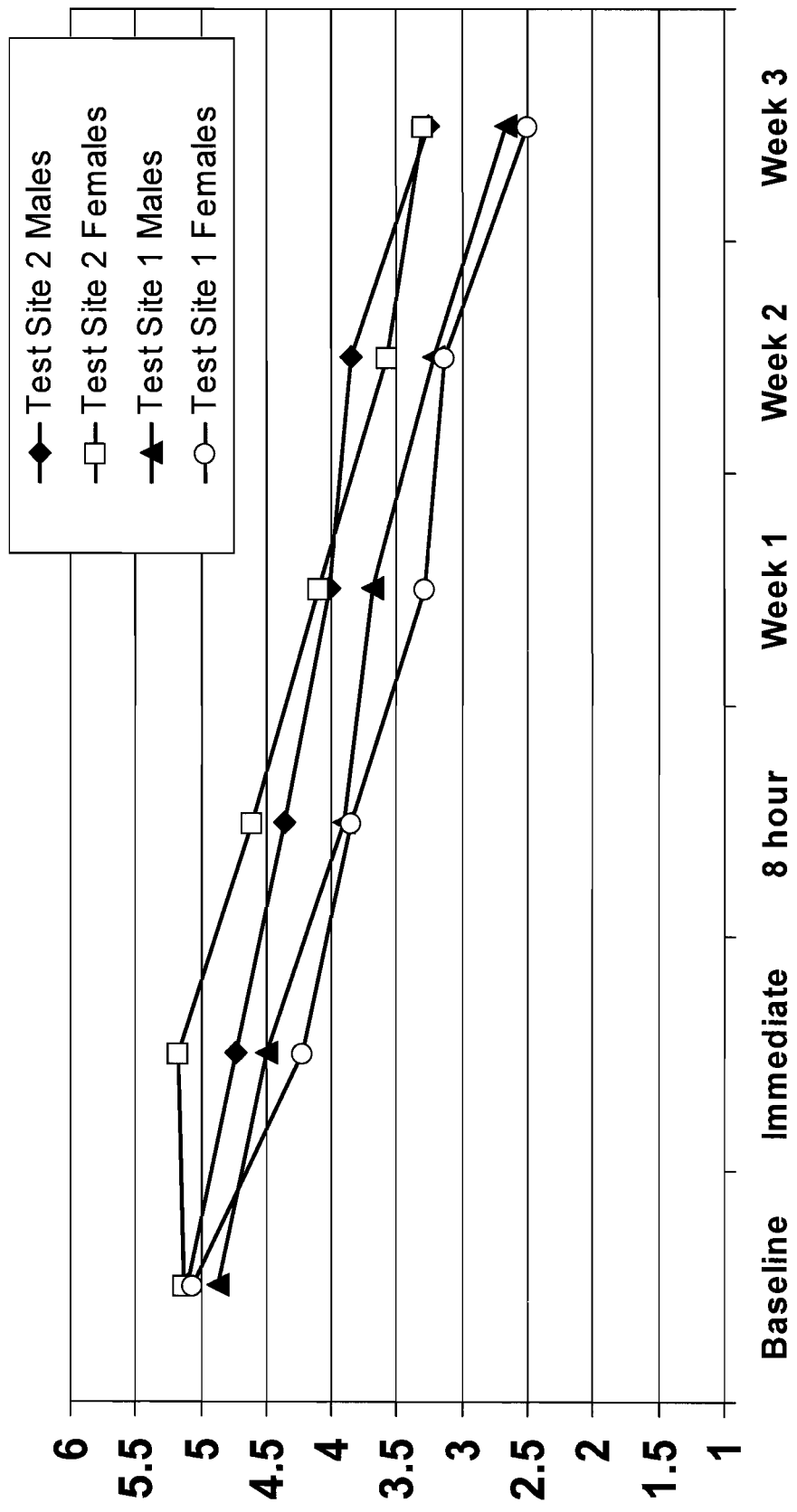
FIG. 6C is a line graph of the test results for subjects having arthritis pain in the knee.

FIG. 6C shows a line graph of the test results for males and females at each test site having arthritis pain in the knee. The x-axis shows the amount of time that subjects used embodiments of the exemplary footwear insole, and the y-axis shows the evaluated VAS scores. As shown, the VAS scores for both males and females continue to decrease with continued use of embodiments of the exemplary footwear insole, as compared to the baseline VAS scores, providing immediate, all day, and sustained pain relief from the arthritis pain in the knee after one minute, eight hours, one week, two weeks, and three weeks.

Based on the combined data for both testing sites shown in FIGS. 6A to 6C, subjects having arthritis pain in the knee experienced statistically significant reductions in knee arthritis pain after using embodiments of the exemplary footwear insole for one minute, eight hours, one week, two weeks, and three weeks, providing immediate, all day, and sustained pain relief from the arthritis pain in the knee.

FIG. 7A shows the test results for subjects having arthritis pain in the foot. FIG. 7A includes data points for the baseline VAS scores and VAS scores after one minute, eight hours, one week, two weeks, and three weeks of using embodiments of the exemplary footwear insole. All the data are considered statistically significant based on the above criteria.

FIG. 7B shows the test results for subjects having arthritis pain in the foot, broken down by testing site. Similar to FIG. 7A, for each group of subjects, an initial baseline VAS score was determined. FIG. 7B includes data points for the VAS scores after one minute, eight hours, one week, two weeks, and three weeks of using embodiments of the exemplary footwear insole. As shown, the data for both males and females at both test site 1 and test site 2 showed immediate, all day, and sustained pain relief of the arthritis pain in the knee, and this data is considered statistically significant based on the above criteria.

Figure 7C:
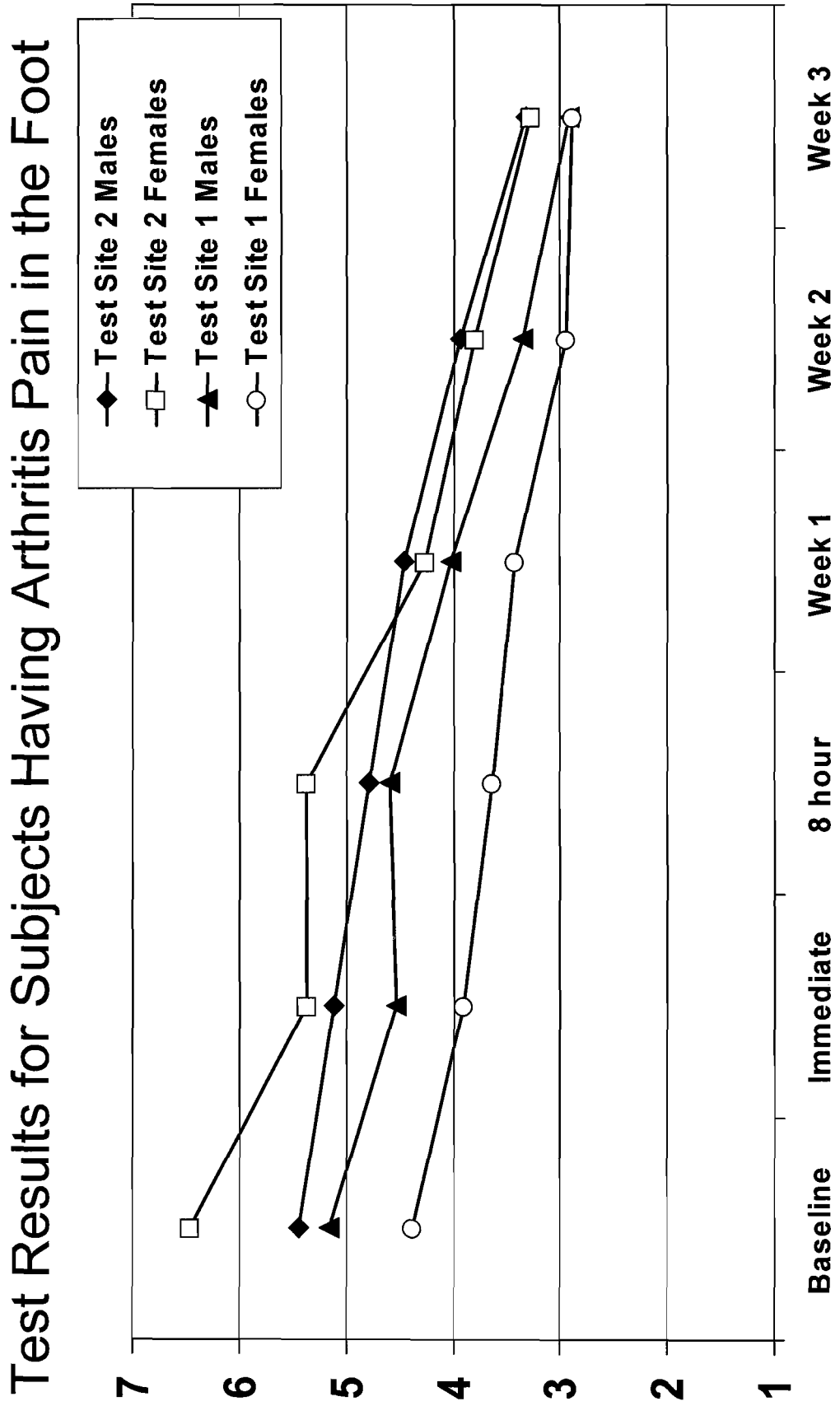
FIG. 7C is a line graph of the test results for subjects having arthritis pain in the foot.

FIG. 7C shows a line graph of the test results for males and females at each test site having arthritis pain in the foot. The x-axis shows the amount of time that subjects used embodiments of the exemplary footwear insole, and the y-axis shows the evaluated VAS scores. As shown, the VAS scores for both males and females continue to decrease with continued use of embodiments of the exemplary footwear insole, as compared to the baseline VAS scores, providing immediate, all day, and sustained pain relief from the arthritis pain in the knee after one minute, eight hours, one week, two weeks, and three weeks.

Based on the combined data for both testing sites shown in FIGS. 7A to 7C, subjects having arthritis pain in the foot experienced statistically significant reductions in foot arthritis pain after using embodiments of the exemplary footwear insole for one minute, eight hours, one week, two weeks, and three weeks, providing immediate, all day, and sustained pain relief from the arthritis pain in the foot.

FIG. 8A shows the test results for subjects having arthritis pain in the hip. FIG. 8A includes data points for the baseline VAS scores and VAS scores after one minute, eight hours, one week, two weeks, and three weeks of using embodiments of the exemplary footwear insole. All the data are considered statistically significant based on the above criteria.

FIG. 8B shows the test results for subjects having arthritis pain in the hip, broken down by testing site. Similar to FIG. 8A, for each group of subjects, an initial baseline VAS score was determined. FIG. 8B includes data points for the VAS scores after one minute, eight hours, one week, two weeks, and three weeks of using embodiments of the exemplary footwear insole. As shown, the data for females at both test sites showed immediate, all day, and sustained pain relief of the arthritis pain in the knee, and this data is considered statistically significant based on the above criteria. In addition, the data for males at test site 1 also showed statistically significant immediate, all day, and sustained pain relief of the arthritis pain in the knee. Further, the data for males at test site 2 generally showed reduced VAS scores compared to the baseline VAS score, but this data included only a small number of samples, n=9.

Figure 8C:
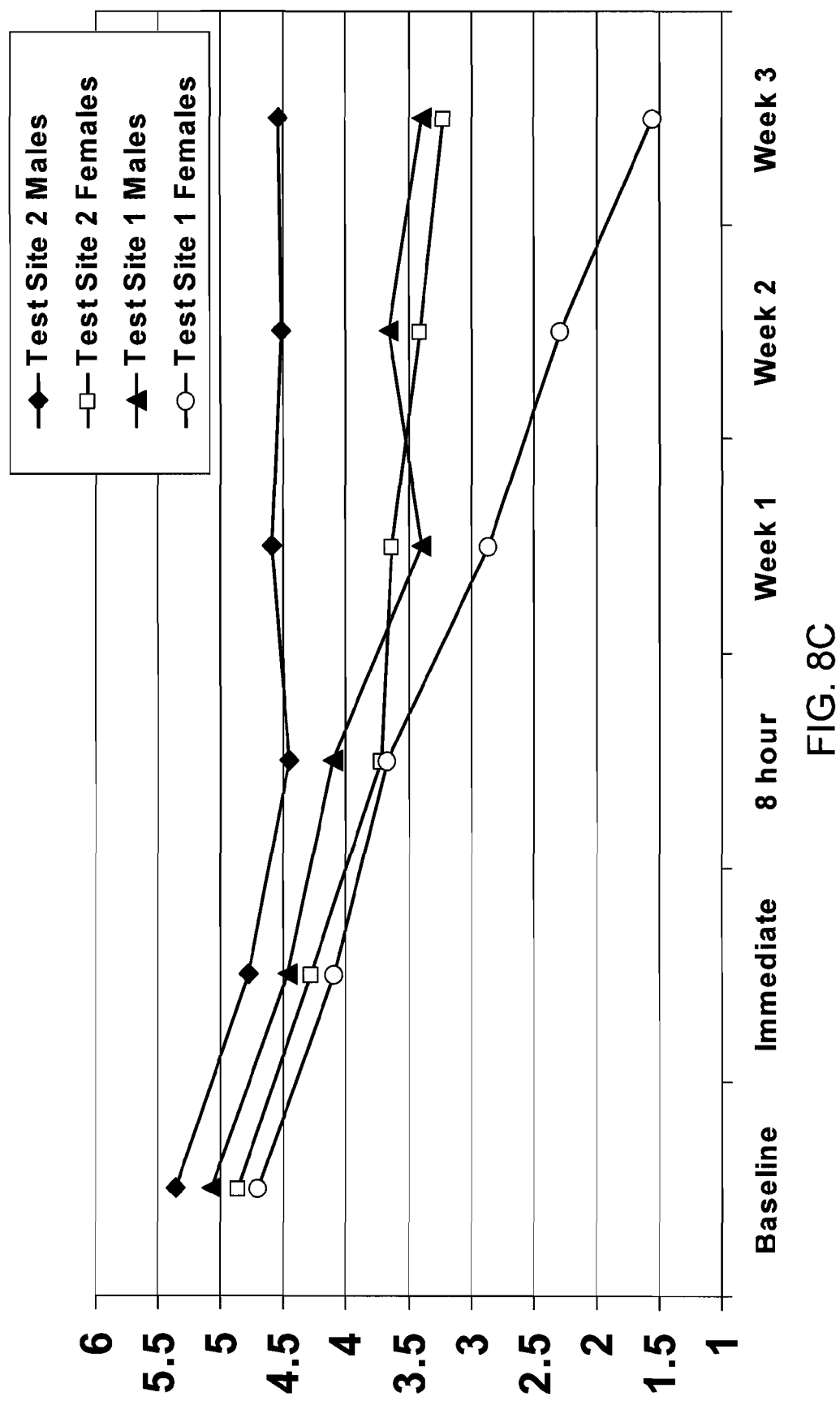
FIG. 8C is a line graph of the test results for subjects having arthritis pain in the hip.

FIG. 8C shows a line graph of the test results for males and females at each test site having arthritis pain in the hip. The x-axis shows the amount of time that subjects used embodiments of the exemplary footwear insole, and the y-axis shows the evaluated VAS scores. As shown, the VAS scores for both males and females continue to decrease with continued use of embodiments of the exemplary footwear insole, as compared to the baseline VAS scores, providing immediate, all day, and sustained pain relief from the arthritis pain in the hip.

Based on the combined data for both testing sites shown in FIGS. 8A to 8C, female subjects and some male subjects having arthritis pain in the hip experienced statistically significant reductions in hip arthritis pain after using embodiments of the exemplary footwear insole for one minute, eight hours, one week, two weeks, and three weeks, providing immediate, all day, and sustained pain relief from the arthritis pain in the hip.

The foregoing description discloses only non-limiting embodiments of the present invention. Modification of the above-disclosed footwear insole, as well as methods for making and using the same, which fall within the scope of the invention, will be readily apparent to those of ordinary skill in the art.

Accordingly, while the present invention has been disclosed in connection with the above non-limiting embodiments, it should be understood that other embodiments may fall within the spirit and scope of the invention, as defined by the following claims.

What is claimed is:

1. An insole for alleviating arthritis pain of at least one of a foot, knee, and hip, comprising:
    a heel portion, an arch portion, and a forefoot portion;
    the heel portion comprising an interior heel portion and a perimeter heel portion;
    the arch portion comprising an interior arch portion and a perimeter arch portion; and
    an upper cushioning layer, a lower cushioning layer, and a rigid shell layer therebetween, the rigid shell layer spanning the heel portion and the arch portion,
    wherein:
        the rigid shell layer includes an upper surface of the rigid shell layer, a lower surface of the rigid shell layer, and a shell aperture within a closed perimeter of the rigid shell layer, wherein the shell aperture extends forward from a calcaneus to metatarsals in a medial arch region such that the shell layer provides support along the perimeter heel portion and the perimeter arch portion and the aperture allows for cushioning of the interior heel portion and the interior arch portion;
        the upper cushioning layer is adhered in part to the upper surface of the rigid shell layer;
        the lower cushioning layer is adhered in part to the lower surface of the rigid shell layer;
        the lower cushioning layer includes an arch support region, a heel support region, a forefoot support region, and a lower layer aperture under the calcaneus of the foot; and
        a portion of the upper cushioning layer extends through a portion of the shell aperture and extends through a portion of the lower layer aperture.

2. The insole of claim 1, wherein the rigid shell layer is configured to support the metatarsals in the medial arch region of the foot.

3. The insole of claim 1, wherein the insole has a topcloth adhered to an upper surface of the upper cushioning layer.

4. The insole of claim 3, wherein the topcloth is polyester.

5. The insole of claim 1, wherein the upper cushioning layer and the lower cushioning layer are polyurethane foam.

6. The insole of claim 1, wherein the rigid shell layer is polypropylene.

7. The insole of claim 3, wherein the topcloth and the upper cushioning layer are coterminous in lateral and longitudinal dimensions.

8. The insole of claim 7, wherein the longitudinal dimensions of the topcloth and the upper cushioning layer extend approximately from the calcaneus to the metatarsals of the foot.

9. The insole of claim 3, wherein the lower cushioning layer has a longitudinal dimension less than a shorter of a longitudinal dimension of the topcloth and a longitudinal dimension of the upper cushioning layer.

10. The insole of claim 3, wherein the rigid shell layer has a longitudinal dimension less than a shorter of a longitudinal dimension of the topcloth, the upper cushioning layer, and the lower cushioning layer.

11. The insole of claim 10, wherein the upper cushioning layer completely covers the upper surface of the rigid shell layer, and the lower cushioning layer completely covers the lower surface of the rigid shell layer.

12. The insole of claim 1, wherein the lower cushioning layer has a varying thickness.

13. The insole of claim 12, wherein the arch support region has greater thickness than at least one of the heel support region and the forefoot support region.

14. The insole of claim 1, wherein at least one of the rigid shell layer, the lower cushioning layer, and the upper cushioning layer is contoured to provide arch support.

15. The insole of claim 1, wherein at least one of the rigid shell layer, the lower cushioning layer, and the upper cushioning layer is contoured to provide heel support.

16. The insole of claim 15, wherein the heel support is a heel cup.

17. The insole of claim 1, wherein a lower surface of the upper cushioning layer is contoured to receive the upper surface of the rigid shell layer.

18. The insole of claim 1, wherein the upper cushioning layer, the rigid shell layer, and the lower cushioning layer are adhered together, and wherein the portion of the upper cushioning layer extending through the shell aperture and the lower layer aperture is mated with the lower cushioning layer.

19. The insole of claim 1, wherein the rigid shell layer provides support for at least one of a first metatarsal and a second metatarsal of the foot.

20. The insole of claim 1, wherein the lower cushioning layer is configured to contact an inner sole of a shoe.

21. The insole of claim 1, wherein the insole is a removable device for insertion in footwear.

22. The insole of claim 1, wherein the insole is integrated in a footwear device.

* * * * *